United States Patent [19]

Cordi et al.

[11] Patent Number: 5,288,905
[45] Date of Patent: Feb. 22, 1994

[54] GLYCYL UREA DERIVATIVES AS ANTI-CONVULSANTS

[75] Inventors: Alex A. Cordi, Suresnes, France; Claude L. Gillet, Blanmont, Belgium

[73] Assignee: G. D. Searle & Co., Chicago, Ill.

[21] Appl. No.: 761,111

[22] Filed: Sep. 17, 1991

Related U.S. Application Data

[63] Continuation of Ser. No. 255,186, Oct. 7, 1988, abandoned.

[51] Int. Cl.$^5$ .......................................... C07C 275/48
[52] U.S. Cl. ........................................ 564/44; 564/45; 564/46
[58] Field of Search ............................. 564/44, 45, 46; 514/594

[56] References Cited

U.S. PATENT DOCUMENTS

| | | | |
|---|---|---|---|
| 2,203,506 | 6/1940 | Piggott et al. | 564/44 |
| 3,821,249 | 7/1974 | Malen et al. | 260/327 B |
| 3,856,857 | 12/1974 | Beregi et al. | 564/44 |
| 3,919,091 | 11/1975 | Eckert et al. | 564/45 |
| 4,025,651 | 5/1977 | Kirino et al. | 424/320 |
| 4,172,943 | 10/1979 | Zaugg et al. | 544/126 |
| 4,639,468 | 1/1987 | Roncucci et al. | 514/620 |

FOREIGN PATENT DOCUMENTS

| | | |
|---|---|---|
| 636245 | 8/1963 | Belgium . |
| 706262 | 11/1967 | Belgium . |
| 4583 | 3/1966 | Japan . |
| 1181673 | 2/1970 | United Kingdom . |

OTHER PUBLICATIONS

Kunitake et al., *Chemistry Letters*, 1984, pp. 1089–1092.
Fischer et al., *Chem. Abs.*, vol. 80: 103937s (1974).
Kunitake et al., *Chem. Abs.*, vol. 106: 183029r (1987).
M. Verderame, *J. Med. Chem.*, 9(1), 153–154 (1966).
M. Verderame, *J. Med. Chem.*, 11(5), 1090 (1968).
S. S. Parmar et al, *J. Pharm. Sci.*, 61(9), 1366–1369 (1972).
S. Nagar et al, *Indian J. Pharm.*, 34(2), 45–47 (1972).
V. K. Agarwal et al, *J. Prakt. Chem.*, 312(5), 964–967 (1970).
T. Takahashi et al, *Yakugaku Zasshi*, 86(10), 958–960 (1966).
P. Truitt et al, *J. Med. Chem.*, 13(3), 574 (1970).
R. M. Peck et al, *J. Med. Chem.*, 19(12), 1422–1423 (1976).
B. Wysocka-Skrzela, *Pol. J. Chem.*, 56(10–12), 1573–1576 (1982).
A. G. de Vazquez et al, *Anales Assoc. Quim. Argentina*, 60, 501–507 (1972).
E. C. Taylor et al, *J. Am. Chem. Soc.*, 103, 7743–7752 (1981).

*Primary Examiner*—Richard L. Raymond
*Assistant Examiner*—Scott C. Rand
*Attorney, Agent, or Firm*—J. Timothy Keane; Joseph W. Bulock

[57] ABSTRACT

A class of glycyl urea derivatives is described having use in treatment of CNS dysfunctions such as epilepsy and convulsive disorders. Compounds of interest are those of the formula

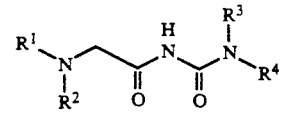

wherein each of $R^1$, $R^2$, $R^3$ and $R^4$ is a group independently selected from hydrido, alkyl, aralkyl, aryloxyalkyl and arylthioalkyl, any one of which groups having a substitutable position may be substituted with one or more radicals selected from halo, alkyl of one to about ten carbon atoms, alkenyl of two to about ten carbon atoms, alkynyl of two to about ten carbon atoms, haloalkyl, alkoxy, alkylthio, alkylsulfinyl and alkylsulfonyl; or a pharmaceutically-acceptable salt thereof; with the proviso that when each of $R^1$ and $R^2$ is ethyl, then $R^3$ and $R^4$ cannot be hydrido simultaneously.

4 Claims, No Drawings

GLYCYL UREA DERIVATIVES AS ANTI-CONVULSANTS

This is a continuation of application Ser. No. 07/255,186 filed Oct. 7, 1988, now abandoned.

FIELD OF THE INVENTION

This invention is in the field of clinical neurology and relates to a class of compounds, compositions and methods useful for treatment of Central Nervous System (CNS) dysfunctions. Of particular interest is a class of glycyl urea compounds for use as anti-convulsants and in management of epilepsy.

BACKGROUND OF THE INVENTION

Convulsive disturbances are typically observed in humans as rapidly alternating contractions and relaxations of muscles which are manifested by irregular movements of the limbs or body and typically accompanied by unconsciousness. The most common cause of convulsions in human adults is epilepsy. Convulsive seizures occur in children from a variety of causes. Convulsions in children may be due to brain damage from birth injuries, or due to dietary deficiencies such as a lack of vitamin D, or due to metabolic disorders such as hypoglycemia or hypokalemia, or due to a sudden body temperature elevation caused by infections such as pneumonia. Convulsions may also be initiated by brain diseases such as meningitis, encephalitis or tumors, and also by conditions brought on by asphyxia or skull fracture.

Certain 1,4-disubstituted piperazines, namely, arylpiperazine-1-oxo-ethylurea have been evaluated for anti-convulsant activity against pentylenetetrazole-induced convulsions, one such compound being 1-[2-(4-phenylpiperazino)-1-oxoethyl]urea [M. Verderame, *J. Med. Chem.*, 9(1), 153–154 (1966)] and another such compound being 1-{2-[4-(p-chlorophenyl)piperazino]-1-oxoethyl}urea [M. Verderame, *J. Med. Chem.*, 11(5), 1090 (1968)]. Other types of substituted carbamides, namely, 1-substituted acetyl-3-aryl carbamides have been evaluated for anti-convulsant activity against pentylenetetrazole-induced seizures, including such compounds as 1-(N-acetylpyrrolidino)-3-aryl carbamides, 1-(N-acetylpiperidino)-3-aryl carbamides and 1-(N-acetylmorpholino)-3-aryl carbamides [S. S. Parmar et al, *J. Pharm. Sci.*, 61(9), 1366–1369 (1972)]. Certain 1-(substituted 2-aminoacetyl benzothiazolyl)-3-arylurea compounds have been evaluated for anticonvulsant properties and for effects of the compounds on pentobarbitone-induced hypnosis in mice, an example of one such compound being 1-(2-aminoacetyl benzothiazolyl)-3-(3-methylphenyl)urea [S. Nagar et al., *Indian J. Pharm.*, 34(2), 45–47 (1972)]. Other arylpiperazine-1-oxo-ethylurea compounds have been shown both to depress and to stimulate central nervous system activity [V. K. Agarwal et al., *J. Prakt. Chem.*, 312(5), 964–966 (1970)]. Certain 1-indanylurea and 2-indanylurea derivatives have been evaluated for analgesic activity, examples of such compounds being 1-(1-indanyl)-3-(2-dimethylamino-1-oxoethyl)urea [T. Takahashi et al., Japanese Appl. No. 4583 of 29 Oct. 62] and 1-(2-indanyl)-3-(2-dimethylamino-1-oxoethyl)urea [T. Takahashi et al., *Yakugaku Zasshi*, 86(10), 958–960 (1966)].

Acetamide derivatives have been investigated for various CNS uses. For example, Belgian Patent No. 706,262 describes a class of tricyclic compounds, namely, diphenylenemethane amine and amide derivatives, mentioned for use as anti-convulsants, as well as for anti-depressive, anti-inflammatory and analgesic uses. U.S. Pat. No. 3,821,249 describes another series of tricyclic-type dibenzothiazepin derivatives asserted to possess psychostimulant, anti-depressive, analgesic, anti-tussive, anti-histaminic and gastric anti-secretory properties. U.S. Pat. No. 4,639,468 describes a class of 2-amino-acetamide derivatives, having use in treatment of epilepsy, dyskinesia such as Parkinsonism, memory troubles and psychic disorders such as depression, with mention in particular of the compound diphenylpropylacetamide.

Various urea or acetamide derivative compounds have been investigated for other pharmaceutical uses. Certain glycylurea derivatives, namely, 1-alkyl-3-dialkylglycyl urea compounds, have been evaluated for antibacterial, anti-inflammatory diuretic shistosomiasis and trichomonicidal properties [P. Truitt et al., *J. Med. Chem.*, 13(3), 574 (1970)]. For example, U.K. Patent No. 1,181,673 describes a series of tricyclic xanthen and thiaxanthen urea derivatives having utility in treatment of peptic ulceration. Carcinogenicity studies have been carried out involving a family of N-(9-acridinyl)glycylglycylglycine compounds [R. M. Peck et al, *J. Med. Chem.*, 19 (12), 1422–1423 (1976)]. A family of acridinylglycine derivatives has been reported to have tumor-inhibiting properties [B. Wysocka-Skrzela, *Pol. J. Chem.*, 56 (10–12), 1573–1576 (1982)]. Belgian Patent No. 636,245 describes a family of 2-($\omega$-alkoxycarbonylalkylideneamino)acetamides having pharmaceutical properties.

Diphenylmethylaminoacetic acid derivatives have been described as intermediates or end products of various laboratory-scale synthetic methods, without mention of pharmaceutical utility: For example, a series of N-benzhydrylaminoacetic acid compounds have been synthesized as intermediates for preparation of N-benzhydrylaminoacetic acid esters or derivatives, two such intermediates being 2-(diphenylmethylamino)acetamide and 2-[di-(para-methoxyphenyl)methylamino]acetamide [A. G. de Vazquez et al, *Anales Asoc. Quim. Argentina*, 60, 501–507 (1972)]. The compound α-diphenylmethylaminoacetamide was incidentally sythesized as a by-product in a multi-step preparation of a series of 3-oxo-1,2-diazetidinium ylides [E. C. Taylor et al, *J. Am. Chem. Soc.*, 103, 7743–7752 (1981)].

Other types of urea and acetamide derivatives, such as glycinamide compounds, have been described for various purposes. For example, U.S. Pat. No. 2,203,506 describes certain ureidoalkylpyridinium and pyridinium acetyl urea compounds for use as textile treatment materials and shows, in particular, the compound diethylaminoacetyl urea as an intermediate in preparation of these pyridinium compounds. German Patent No. 2,511,311 describes a family of glycinamides for use as fungicides.

DESCRIPTION OF THE INVENTION

Treatment of a mammal afflicted with or susceptible to a CNS disorder, such as epilepsy, depression, convulsions, dyskinesia, cognitive disorder or other neurodegenerative disease or neurotoxic injury, is provided by administering to the mammal a therapeutically-effective amount of a compound selected from a class of glycyl urea compounds defined by Formula I:

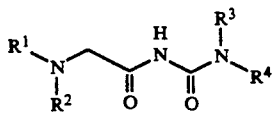

(I)

wherein each of $R^1$, $R^2$, $R^3$ and $R^4$ is a group independently selected from hydrido, alkyl, aralkyl, aryloxyalkyl and arylthioalkyl, any one of which groups having a substitutable position may be substituted with one or more radicals selected from halo, alkyl of one to about ten carbon atoms, alkenyl of two to about ten carbon atoms, alkynyl of two to about ten carbon atoms, haloalkyl, alkoxy, alkylthio, alkylsulfinyl and alkylsulfonyl; or a pharmaceutically-acceptable salt thereof; with the proviso that when each of $R^1$ and $R^2$ is ethyl, then $R^3$ and $R^4$ cannot be hydrido simultaneously.

It is believed that the compounds defined by Formula I are novel where the Formula I definition is qualified by the proviso that at least one of $R^1$ and $R^2$ is a group other than hydrido and with the further proviso that at least one of $R^3$ and $R^4$ is a group other than hydrido.

It is believed that novel pharmaceutical compositions, as well as novel methods of therapeutic treatment, are provided wherein a therapeutically-effective compound is selected, for inclusion in the composition or for use in the treatment, from the class of compounds defined by Formula I without qualification of Formula I with any of the foregoing proviso descriptions.

A preferred class of compounds within Formula I consists of those compounds wherein each of $R^1$, $R^2$, $R^3$ and $R^4$ is a group independently selected from hydrido, alkyl and alkyl substituted with one or more radicals selected from halo, alkenyl of two to about ten carbon atoms, haloalkyl, alkoxy, alkylthio, alkylsulfinyl and alkylsulfonyl; wherein each of $R^1$, $R^2$, $R^3$ and $R^4$ is a group further selected from aralkyl and aralkyl substituted on the aryl portion with one or more radicals selected from halo, alkyl of one to about ten carbon atoms, alkenyl of two to about ten carbon atoms, haloalkyl, alkoxy, alkylthio, alkylsufinyl and alkylsulfonyl; and wherein each of $R^1$, $R^2$, $R^3$ and $R^4$ is a group further selected from aryloxyalkyl and aryloxyalkyl substituted with one or more radicals selected from halo alkyl of one to about ten carbon atoms, alkenyl of two to about ten carbon atoms, alkynyl of two to about ten carbon atoms, haloalkyl, alkoxy, alkylthio, alkylsulfinyl and alkylsulfonyl; or a pharmaceutically-acceptable salt thereof.

A further preferred class of compounds within Formula I consists of those compounds wherein each of $R^1$, $R^2$, $R^3$ and $R^4$ is a group independently selected from hydrido, alkyl and alkyl substituted with one or more radicals selected from halo, alkenyl of two to about ten carbon atoms, haloalkyl, alkoxy, alkylthio, alkylsulfinyl and alkylsulfonyl; wherein each of $R^1$, $R^2$, $R^3$ and $R^4$ is a group further selected from aralkyl and aralkyl substituted on the aryl portion with one or more radicals selected from halo, alkyl of one to about ten carbon atoms, alkenyl of two to about ten carbon atoms, haloalkyl, alkoxy, alkylthio, alkylsufinyl and alkylsulfonyl; or a pharmaceutically-acceptable salt thereof.

A further preferred class of compounds within Formula I consists of those compounds wherein each of $R^1$, $R^2$, $R^3$ and $R^4$ is a group independently selected from hydrido, alkyl and alkyl substituted with one or more radicals selected from halo, haloalkyl, alkoxy, alkylthio, alkylsulfinyl and alkylsulfonyl; wherein each of $R^1$, $R^2$, $R^3$ and $R^4$ is a group further selected from aralkyl and aralkyl substituted on the aryl portion with one or more radicals selected from halo, alkyl of one to about ten carbon atoms, haloalkyl, alkoxy, alkylthio, alkylsufinyl and alkylsulfonyl; or a pharmaceutically-acceptable salt thereof.

A more preferred class of compounds of Formula I consists of those compounds wherein each of $R^1$, $R^2$, $R^3$ and $R^4$ is a group independently selected from hydrido, alkyl of one to about twenty carbon atoms and alkyl of one to about twenty carbon atoms substituted with one or more radicals selected from halo, haloalkyl having an alkyl portion of one to about ten carbon atoms and alkoxy having an alkyl portion of one to about ten carbon atoms; wherein each of $R^1$, $R^2$, $R^3$ and $R^4$ is a group further selected from aralkyl having an alkyl portion of one to about ten carbon atoms and aralkyl having an alkyl portion of one to about ten carbon atoms substituted on the aryl portion with one or more radicals selected from halo, alkyl of one to about ten carbon atoms, haloalkyl having an alkyl portion of one to about ten carbon atoms and alkoxy having an alkyl portion of one to about ten carbon atoms; or a pharmaceutically-acceptable salt thereof.

An even more preferred class of compounds of Formula I consists of those compounds wherein each of $R^1$, $R^2$, $R^3$ and $R^4$ is a group independently selected from hydrido, linear alkyl of one to about twelve carbon atoms, aralkyl having a linear alkyl portion of one to about five carbon atoms and aralkyl having a linear alkyl portion of one to about five carbon atoms, the aryl portion of which may be substituted with one or more halo radicals; or a pharmaceutically-acceptable salt thereof.

A highly preferred class of compounds of Formula I consists of those compounds wherein each of $R^1$, $R^2$, $R^3$ and $R^4$ is a group independently selected from hydrido, methyl, ethyl, n-propyl, n-butyl, n-pentyl, n-hexyl, n-heptyl, n-octyl, n-nonyl, n-decyl, n-undecyl and n-dodecyl, any one of which groups having a substitutable position may be substituted with one or more radicals selected from phenyl and halophenyl; or a pharmaceutically-acceptable salt thereof.

A more highly preferred class of compounds within Formula I consists of those compounds wherein each of $R^1$, $R^2$, $R^3$ and $R^4$ is a group independently selected from hydrido, methyl, ethyl, n-propyl, n-butyl, n-pentyl, n-hexyl, n-heptyl, n-octyl, n-nonyl, n-decyl, n-undecyl, n-dodecyl, benzyl, diphenylmethyl, phenylethyl, diphenylpropyl, phenylbutyl, diphenylbutyl, phenylpentyl and diphenylpentyl, any one of which phenyl-containing groups may be substituted on the phenyl portion with one or more fluoro or chloro groups; or a pharmaceutically-acceptable salt thereof.

A most highly preferred class of compounds within Formula I consists of those compounds wherein each of $R^1$, $R^2$, $R^3$, and $R^4$ is a group independently selected from hydrido, methyl, ethyl, n-propyl, n-butyl, n-pentyl, n-hexyl, n-heptyl, n-octyl, n-nonyl, n-decyl, n-undecyl, n-dodecyl, benzyl, diphenylmethyl, phenylethyl, diphenylpropyl; or a pharmaceutically-acceptable salt thereof.

The term "hydrido" denotes a single hydrogen atom (H). The term "alkylene" embraces a methylene group, i.e., a —$CH_2$— group, or a series or chain of two or more methylene groups —$CH_2$—$(CH_2)_{\overline{n}}$ wherein "n" is a whole number selected from two through about five, which chain is characterized in being divalent and containing no unsaturation, an example of which is an ethylene group (—CH$_2$CH$_2$—). Where the term "alkyl" is used, either alone or within other terms such as "haloalkyl", "aralkyl" and "hydroxyalkyl", the term "alkyl" embraces linear or branched radicals having one to about ten carbon atoms unless otherwise specifically described. Preferred alkyl radicals are "lower alkyl" radicals having one to about five carbon atoms. The term "cycloalkyl" embraces radicals having three to about ten carbon atoms, such as cyclopropyl, cyclobutyl, cyclohexyl and cycloheptyl. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. Examples of a dihaloalkyl group are dibromomethyl, dichloromethyl and bromochloromethyl. Examples of a polyhaloalkyl are trifluoromethyl, 2,2,2-trifluoroethyl, perfluoroethyl and 2,2,3,3-tetrafluoropropyl groups. The term "alkoxy", embraces linear or branched oxy-containing radicals having an alkyl portion of one to about ten carbon atoms, such as methoxy, ethoxy, isopropoxy and butoxy. The term "alkylthio" embraces radicals containing a linear or branched alkyl group, of one to about ten carbon atoms, attached to a divalent sulfur atom, such as a methylthio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "sulfinyl" and "sulfonyl", whether used alone or linked to other terms, denote, respectively, the divalent radicals =SO and =SO$_2$.

Within this class of glycyl urea compounds of the invention are the pharmaceutically-acceptable salts of the compounds of Formula I, including acid addition salts and base addition salts. The term "pharmaceutically-acceptable salts" embraces salts commonly used to form addition salts of free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methanesulfonic, ethanesulfonic, 2-hydroxyethanesulfonic, pantothenic, benzenesulfonic, toluenesulfonic, sulfanilic, mesylic, cyclohexylaminosulfonic, stearic, alginic, β-hydroxybutyric, malonic, galactaric and galacturonic acid. Suitable pharmaceutically-acceptable base addition salts of compounds of Formula I include metallic salts made from calcium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula I can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereomeric salts by treatment of the racemic mixture with an optically active acid or base. Examples of appropriate acids are tartaric, diacetyltartaric, dibenzoyltartaric, ditoluoyltartaric and camphorsulfonic acid. Then, the mixture of diastereomers may be resolved by crystallization followed by liberation of the optically active bases from these salts. A different process for separation of optical isomers involves the use of a chiral chromatography column optimally chosen to maximize the separation of the enantiomers. Still another available method involves synthesis of covalent diastereomeric molecules by reacting compounds of Formula I with an optically pure acid in an activated form or an optically pure isocyanate. The synthesized diastereomers can be separated by conventional means such as chromatography, distillation, crystallization or sublimation, and then hydrolyzed to deliver the enantiomerically pure compound. The optically active compounds of Formula I can likewise be obtained by utilizing optically active starting materials. These isomers may be in the form of a free acid, a free base, an ester or a salt. All of these stereoisomers, optical isomers, diastereomers, as well as mixtures thereof such as racemic mixtures, are within the scope of the invention.

GENERAL SYNTHETIC PROCEDURES

Compounds within Formula I can be synthesized in accordance with the following general procedures wherein for each formula shown the substitution pattern for R$^1$, R$^2$, R$^3$ and R$^4$ is as defined before:

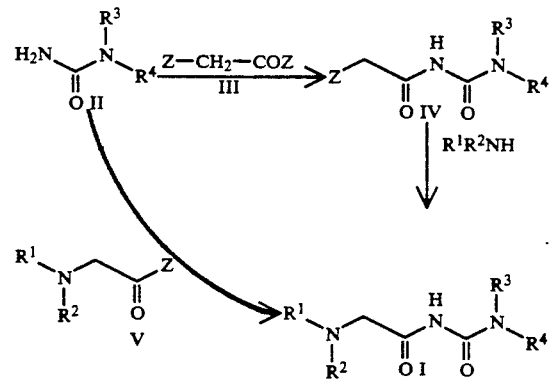

Compounds of the invention I may be synthesized by reacting urea II with a reactant of structure III wherein Z represents a good leaving group such as an halogen, a tosyl group, a mesityl group, or an acyloxy group, susceptible to be substituted by urea or amine groups.

This reaction is best conducted neat or in an aprotic, non-nucleophilic solvent such as chlorinated hydrocarbon solvents exemplified by chloroform and methylene chloride, ethers such as dioxan and tetrahydrofuran, carboxamide and phosphoramide solvents such as dimethylformamide and hexamethylphosphortriamide at a temperature between room temperature and the reflux temperature of the solvent.

Intermediate IV is then reacted with an amine of general formula $R^1R^2NH$ in a solvent of a type described above or an alcohol such as methanol, ethanol or isopropanol with the temperature of the reaction being kept between room temperature and the reflux temperature of the solvent. The reaction may be conducted in the presence of an acid quencher such as a non-nucleophilic amine exemplified by triethylamine, or an inorganic base such as sodium bicarbonate or potassium carbonate in the presence, optionally, of a phase-transfer catalyst.

An alternate method which may be used to synthesize compounds of the invention involves reacting urea of structure II with an amino acid derivative of structure V where Z is a leaving group as described above. The reaction may be conducted in conditions of solvent and temperature as described above.

Table I contains 21 specific compounds within Formula I which can be prepared in accordance with the above-described General Synthetic Procedures:

TABLE I

| Compound # | Formal Name |
| --- | --- |
| 1 | 1-octyl-3-(2-pentylamino-1-oxoethyl)urea |
| 2 | 1-(2-phenylethyl)-3-(2-pentylamino-1-oxoethyl)urea |
| 3 | 1-octyl-3-[2-(2-phenylethyl)amino-1-oxoethyl]urea |
| 4 | 1-octyl-3-(2-octylamino-1-oxoethyl)urea |
| 5 | 1-(2-phenylethyl)-3-[2-(2-phenylethyl)amino-1-oxoethyl]urea |
| 6 | 1-(2-phenylethyl)-3-(2-octylamino-1-oxoethyl)urea |
| 7 | 1-pentyl-3-[2-(2-phenylethyl)amino-1-oxoethyl]urea |
| 8 | 1-pentyl-3-(2-pentylamino-1-oxoethyl)urea |
| 9 | 1-pentyl-3-(2-octylamino-1-oxoethyl)urea |
| 10 | 1-methyl-3-(2-diphenylmethylamino-1-oxoethyl)urea |
| 11 | 1-(2-phenylethyl)-3-(2-diphenylmethylamino-1-oxoethyl)urea |
| 12 | 1-octyl-3-(2-diphenylmethylamino-1-oxoethyl)urea |
| 13 | 1-pentyl-3-(2-diphenylmethylamino-1-oxoethyl)urea |
| 14 | 1,1-dimethyl-3-(2-diphenylmethylamino-1-oxoethyl)urea |
| 15 | 1-methyl-3-(2-octylamino-1-oxoethyl)urea |
| 16 | 1,3-dimethyl-3-(2-diphenylmethylamino-1-oxoethyl)urea |
| 17 | 1,3-dimethyl-3-(2-octylamino-1-oxoethyl)urea |
| 18 | 1,3-dimethyl-3-(2-pentylamino-1-oxoethyl)urea |
| 19 | 1,1-diethyl-3-(2-diphenylmethylamino-1-oxoethyl)urea |
| 20 | 1,1-dipropyl-3-(2-diphenylmethylamino-1-oxoethyl)urea |
| 21 | 1,1-dibutyl-3-(2-diphenylmethylamino-1-oxoethyl)urea |

The following Examples I-VIII are detailed descriptions of the methods of preparation of compounds of Formula I, particularly those listed in Table I. These detailed preparations fall within the scope of, and serve to exemplify, the above described General Synthetic Procedures which form part of the invention. These Examples I-VIII are presented for illustrative purposes only and are not intended as a restriction on the scope of the invention. All parts are by weight unless otherwise indicated.

EXAMPLE I

1-octyl-3-(2-pentylamino-1-oxoethyl)urea

Compound #1

A reaction vessel was charged with 5 g (29 mmole) of octyl-urea to which 10 ml (13 mmole) of chloracetyl chloride was added dropwise at room temperature. The suspension was brought to reflux and held at reflux for one hour. The resulting colorless solution was cooled and the white solid was filtered to provide an intermediate identified as 1-octyl-3-(2-chloro-1-oxoethyl)urea (M.P.=97° C.). A reaction vessel was charged with 5.1 g (20 mmole) of 1-octyl-3-(2-chloro-1-oxoethyl)urea, 1.74 g (20 mmole) of pentylamine, 2.02 g (20 mmole) of triethylamine and 30 ml of toluene. The reaction mixture was brought to reflux and held at reflux for about 4 hours. The resulting suspension was filtered hot and solvent from the filtrate was evaporated. The resulting dark brown oil was diluted with hexane and then HCl-ether was added. The resulting semi-solid was filtered and crystallized twice in ethyl acetate with a few drops of isopropanol.

| | Elementary analysis: | | |
| --- | --- | --- | --- |
| | C | H | N |
| calc. | 57.21 | 10.20 | 12.51 |
| found | 57.05 | 10.45 | 12.29 |

EXAMPLE II

1-octyl-3-[2-(2-phenylethyl)amino-1-oxoethyl]urea

Compound #3

A reaction vessel was charged with 7.5 g (30 mmole) of 1-octyl-3-(2-chloro-1-oxoethyl)urea prepared following Example I, 3.63g (30 mmole) of 2-phenylethylamine, 3.07 g (30 mmole) of triethylamine and 50 ml of toluene. The reaction mixture was brought to reflux and held at reflux for 4 hours. The suspension was filtered hot and solvent from the filtrate was evaporated. Upon addition of ether to the remaining oil, more solid was formed which was filtered. HCl-ether was added to the solution and the ether was evaporated. The residue was stirred in ethyl acetate, the solid was filtered and then crystallized in isopropanol.

| | Elementary analysis: | | |
| --- | --- | --- | --- |
| | C | H | N |
| calc. | 61.69 | 8.72 | 11.36 |
| found | 61.68 | 8.82 | 11.38 |

EXAMPLE III

1-(2-phenylethyl)-3-(2-octylamino-1-oxoethyl)urea

Compound #6

A reaction vessel was charged with 21 g (128 mmole) of (2-phenylethyl)urea. With stirring at room temperature, 70.9 g (630 mmole) of chloracetyl chloride was added to the vessel. The mixture was brought to reflux and held at reflux for half an hour. The brown solution was cooled and the resulting solid was filtered and washed with ethyl acetate to provide an intermediate identified as 1-(2-phenylethyl)-3-(2-chloro-1-oxoethyl)urea (M.P.=135° C.). A reaction vessel was charged with 9.6 g (40 mmole) of 1-(2-phenylethyl)-3-(2-chloro-1-oxoethyl)urea, 5.2 g (40 mmole) of octylamine, 4.04 g (40 mmole) of triethylamine and 70 ml of toluene. The resulting suspension was brought to reflux and held at reflux for 5 hours. Solvent was evaporated under reduced pressure, the residue was diluted with ether, the insoluble material was filtered and then HCl-ether was added to the filtrate. The newly-formed solid was filtered and then crystallized in isopropanol.

| | Elementary analysis: | | |
|---|---|---|---|
| | C | H | N |
| calc. | 61.69 | 8.72 | 11.36 |
| found | 61.73 | 8.81 | 11.34 |

EXAMPLE IV 1-pentyl-3-(2-pentylamino-1-oxoethyl)urea

Compound #8

A reaction vessel was charged with 17 g (130 mmole) of pentylurea and 56.72 g (500 mmole) of chloroacetylchloride. The reaction mixture was heated to 120° C. Upon cooling of the mixture, a solid crystallized, which was suspended in hexane, filtered and identified as 1-pentyl-3-(2-chloro-1-oxoethyl)urea (M.P.=110° C.). A reaction vessel was charged with 6 gr (29 mmole) of 1-pentyl-3-(2-chloro-1-oxoethyl)urea, 2.5 g (29 mmole) of pentylamine and 2.9 g (29 mmole) of triethylamine. The reaction mixture was heated at reflux for about 4 hours. The resulting solution was cooled, filtered, diluted with ether, filtered again and thereafter HCl-ether was added. After evaporation of the solvent under reduced pressure, the resulting solid was stirred in ethyl acetate, filtered and crystallized in isopropanol.

| | Elementary analysis: | | |
|---|---|---|---|
| | C | H | N |
| calc. | 53.14 | 9.60 | 14.30 |
| found | 53.17 | 9.75 | 14.21 |

EXAMPLE V 1-(2-phenylethyl)-3-(2-diphenylmethylamino-1-oxoethyl)urea

Compound #11

A reaction vessel was charged with 5 g (21 mmole) of 1-(2-phenylethyl)-3-(2-chloro-1-oxoethyl)urea prepared as described in Example III, 3.81 g (21 mmole) of diphenylmethylamine and 2.12 g (21 mmole) of triethyl amine. The reaction mixture was heated in 25 ml of toluene at 80° C. for about 12 hours. Then, the solution was cooled, diluted with ethyl acetate, washed with water, dryed over magnesium sulfate and solvent was evaporated. The resulting yellow oil was purified by chromatography on a silicagel column eluted with a mixture of chloroform/methanol (97/3). After evaporation of the solvent, product compound was crystallized by addition of pentane.

| | Elementary analysis: | | |
|---|---|---|---|
| | C | H | N |
| calc. | 74.39 | 6.50 | 10.84 |
| found | 74.19 | 6.52 | 10.83 |

Table II contains 11 specific compounds which have been synthesized in accordance with the procedures described in Examples I-V:

TABLE II

| Compound # | R$^1$ | R$^2$ | R$^3$ | R$^4$ | Crystallization Solvents | *M.P. °C. |
|---|---|---|---|---|---|---|
| 1 | C$_5$H$_{11}$— | H | H | C$_8$H$_{17}$— | ethyl acetate-isopropanol | 166* |
| 2 | C$_5$H$_{11}$— | H | H | —CH$_2$—CH$_2$— | isopropanol | 181** |
| 3 | —CH$_2$—CH$_2$— | H | H | C$_8$H$_{17}$— | isopropanol | 180** |
| 4 | C$_8$H$_{17}$— | H | H | C$_8$H$_{17}$— | isopropanol | 162** |
| 5 | —CH$_2$—CH$_2$— | H | H | —CH$_2$—CH$_2$— | ethanol | 197** |
| 6 | C$_8$H$_{17}$— | H | H | —CH$_2$—CH$_2$— | isopropanol | 185.5** |

TABLE II-continued $$R^1\underset{R^2}{\overset{}{N}}-CH_2-\underset{O}{\overset{H}{\underset{||}{N}}}-\underset{O}{\overset{R^3}{\underset{||}{N}}}-R^4$$

| Compound # | R¹ | R² | R³ | R⁴ | Crystallization Solvents | *M.P. °C. |
|---|---|---|---|---|---|---|
| 7 | phenyl-CH₂-CH₂- | H | H | C₅H₁₁— | isopropanol | 177** |
| 8 | C₅H₁₁— | H | H | C₅H₁₁— | isopropanol | 170** |
| 9 | C₈H₁₇— | H | H | C₅H₁₁— | ethyl acetate | 164.5** |
| 10 | diphenyl-CH— | H | H | CH₃— | isopropanol | 150 |
| 11 | diphenyl-CH— | H | H | —CH₂—CH₂—phenyl | silica gel chromatography | 98 |

*M.P. = Melting Point
**Hydrochloride Salt

BIOLOGICAL EVALUATION

Treatment of a mammal afflicted by or susceptible to certain CNS disorders is accomplished by administration of a therapeutically-effective amount of a compound of Formula I. In particular, Compounds #1-11 of Table II were evaluated by in vitro and in vivo animal model assays to determine the pharmacological properties of such compounds and their likely suitability for use as therapeutic drugs in humans. These biological assays, as described below, consisted of prevention of induced convulsions in mice, determination of acute toxicity in mice and animal behavior assays. Except as otherwise specified, the animals used in the in vivo tests were male Swiss albino mice weight 22 to 33 g [CD1, Charles River, France], housed in groups of 10 on a 12-hour dark-light cycle for at least one week before use and fasted overnight prior to testing.

Convulsant-Agent Induced Convulsions

Compounds of Formula I were evaluated as inhibitors of convulsions and death induced by different convulsant agents: 3-mercaptopropionic acid (3-MPA; 120 mg/kg subcutaneously), bicuculline (BIC, 0.6 mg/kg intravenously), pentylenetetrazole (PTZ, 55 mg/kg intravenously) and supramaximal electroconvulsive shocks (ECS evoked by a current intensity of 48 mA, 50 Hz. 0.2 sec duration, 10 msec square pulse, corneal electrodes) [W. van Dorsser, D. Barris, A. Cordi and J. Roba, *Arch. Int. Pharmacodyn.*, 266, 239-249 (1983)]. The compounds of the invention were administered orally at a dosage of either 100 mg/kg or 30 mg/kg in a volume of 10 ml/kg each to 5 mice. Tonic convulsions and the number of dead mice were noted. Results are given in Table III as a score which represents the total number of mice protected from convulsions induced by 3-mercaptopropionic acid at dose of 100 mg/kg for two groups of five animals, or the percentage of mice protected from convulsions induced by bicuculline at a dose of 30 mg/kg for four groups of five animals.

TABLE III

| | | Number of Mice Protected From Convulsions Induced by 3-MPA at 100 mg/kg Interval* | |
|---|---|---|---|
| Compound # | Percentage of Mice Protected from Bicuculline | 30 min | 2 hr |
| 1 | 35 | 0 | |
| 2 | 25 | 3 | |
| 3 | 55 | 6 | 3 |
| 4 | 35 | 4 | 3 |
| 5 | 45 | 6 | 1 |
| 6 | 35 | 9 | 9 |
| 7 | 25 | 1 | |
| 8 | 40 | 0 | |
| 9 | 35 | 7 | 4 |
| 10 | | 1 | |
| 11 | | 0 | |

*Interval of administration of test compound before convulsions induced.

Based upon data generated from the previously-described anti-convulsant experiments, ED₅₀ values were calculated at which Compound #6 inhibits convulsions induced by the convulsant agents listed in Table IV.

TABLE IV

| Convulsant | Inhibition of Convulsions by Cpd. #6 (ED$_{50}$; mg/kg) |
|---|---|
| 3-MPA | 16 |
| ECS | 60 |
| PZT | 56 |

Acute Toxicity

The acute toxicity of compounds of the invention was determined after oral administration of the test compound to mice. Compound to be tested was suspended in a 1% tragacanth gum mucilage, and was administered by means of an intragastric probe to a group of three male mice. Doses used in the test were determined by observing toxic effects on the mice, which doses varied from 3,000 mg/kg down to about 3 mg/kg. The mortality was recorded over a period of 15 days. The LD$_{50}$ results reported in Table V were calculated according to published methods [Lichtfield and Wilcoxon, *J. Pharmacol. Exp. Ther.*, 96, 99 (1949)] and expressed in mg of test compound per kilogram of mouse body weight.

Behavioral Studies

Behavioral effects of compounds of the invention on animals were determined by observations taken at 5 to 6 hours and at 24 hours after administration of compounds in the acute toxicity studies. Determinations were made based on a method derived from that of S. Irwin [See R. A. Turner, *Screening Methods in Pharmacology*, Chapter 3, pages 22–34, Academic Press, N.Y. (1965)]. If an anomaly were noted, the observation was extended and smaller doses were tested. Possible types of behavior to be observed are as follows: analgesia (AAG), convulsions (CON), depression (DEP), exophthalmia (EOP), excitation (EXC), hyperalgesia (HAG), hypothermia (ATH), hypotonia (ATN), piloerection (PIE), palpebral ptosis (PTO), reduction of the pinna reflux (RPI), reduction of the rearing reflex (RRE), reduction of the flexion reflex (RRF), sedation (SED), tremors (TRE), cyanosis (CYA), diarrhea (DIA), increase of the pinna reflex (HPI), increase of the flexion reflex (HRF), dyspnea (DYS), toxic (TOX), zero ("0") means no effect. Behaviors observed are reported in Table V by numbers which represent the dose at which the behavior is observed.

TABLE V

| Compound # | LD$_{50}$ (mg/kg) | Behavior (mg/kg) |
|---|---|---|
| 1 | >1000 | 1000:0 |
| 2 | >1000 | 1000:SED, RPI, RRE |
| 3 | >3000 | 3000:SED, ATN |
| 4 | >3000 | 3000:0 |
| 5 | 1750 | 3000:TOX, DEP |
| 6 | >3000 | 1000:SED, ATN |
| 7 | >3000 | 1000:SED |
| 8 | >3000 | 1000:SED<br>3000:DEP, RPI, ATN |
| 9 | >1000 | 1000:0 |

Chronic Focal Epilepsy Assay

In a model of chronic focal epilepsy where cobalt powder is placed on rat frontal cortex, the animals develop, after several days, chronic expression of afterdischarge-like spike activity which can be recorded by EEG. Compound #6 has, when administered by intraperitoneal route, a threshold dose of 200 mg/kg for inhibiting these spike activities with the effect being observed from 30 to 90 minutes.

5HTP-Induced Head Twitch

Compound #6 was evaluated for inhibition of head twitches produced in mice by administration of L-5-hydroxytryptophan (5HTP, 10 mg/kg intraperitoneously) after nialamide treatment (50 mg/kg intraperitoneal, 22 hours before the test). The head twitches were counted for 45 min. starting 15 min. after 5HTP administration. [E. Friedmann et al.; *Europ. J. Pharmacol.*, 89, 69–76 (1983)]. Compound #6 was given 2 hours before the 5HTP challenge and was found to have, a ED$_{50}$ of 200 mg/kg p.o.

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 300 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

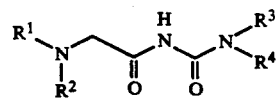

wherein each of $R^1$, $R^2$, $R^3$ and $R^4$ is independently selected from hydrido and aralkyl having an alkyl portion of one to about ten carbon atoms and optionally substituted on the aryl portion with one or more radicals selected from halo, alkyl having one to about ten carbon atoms, haloalkyl having an alkyl portion of one to about ten carbon atoms and alkoxy; or a pharmaceutically-acceptable salt thereof; with the proviso that at least one of $R^1$ and $R^2$ is a group other than hydrido and with the further proviso that at least one of $R^3$ and $R^4$ is a group other than hydrido.

2. Compound of claim 1 wherein each of $R^1$, $R^2$, $R^3$ and $R^4$ is a group independently selected from hydrido, benzyl, diphenylmethyl, phehylethyl, diphenylpropyl, phenylbutyl, diphenylbutyl, phenylpentyl and diphenylpentyl, any one of which phenyl-containing groups may be substituted on the phenyl portion with one or more fluoro or chloro groups; or a pharmaceutically-acceptable salt thereof.

3. Compound of claim 2 selected from 1-(2-phenylethyl)-3-[2-(2-phenylethyl)amino-1-oxoethyl]urea and 1-(2-phenylethyl)-3-[2-diphenylmethylamino-1-oxoethyl]urea.

4. A compound of claim 3 which is 1-(2-phenylethyl)-3-[2-(2-phenylethyl)amino-1-oxoethyl]urea.

* * * * *